United States Patent
Knezevic et al.

(10) Patent No.: US 6,602,661 B1
(45) Date of Patent: Aug. 5, 2003

(54) METHODS AND ARRAYS FOR DETECTING BIOMOLECULES

(75) Inventors: Vladimir Knezevic, Silver Spring, MD (US); Michael R. Emmert-Buck, Silver Spring, MD (US)

(73) Assignees: 20/20 GeneSystems, Inc., Rockville, MD (US); The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/718,990

(22) Filed: Nov. 20, 2000

Related U.S. Application Data

(63) Continuation-in-part of application No. PCT/US00/20354, filed on Jul. 26, 2000.
(60) Provisional application No. 60/145,613, filed on Jul. 26, 1999.

(51) Int. Cl.[7] .................... G01N 33/53; G01N 33/543
(52) U.S. Cl. .................. 435/6; 435/4; 435/7.1; 435/7.9; 435/7.92; 435/174; 435/287.1; 436/518; 436/524; 436/528; 422/68.1; 422/82.01
(58) Field of Search .................. 422/68.1, 82.01; 435/4, 6, 7.1, 7.9, 7.92, 174, 287.1; 436/518, 524, 528

(56) References Cited

U.S. PATENT DOCUMENTS

| | | | |
|---|---|---|---|
| 3,620,947 A | 11/1971 | Allen et al. ............. 204/180 G |
| 4,176,069 A | * 11/1979 | Metz et al. ............. 210/321.75 |
| 4,337,131 A | 6/1982 | Vesterberg ............. 204/180 G |
| 4,613,567 A | 9/1986 | Yasoshima et al. ........... 435/7 |
| 4,716,101 A | 12/1987 | Thompson et al. |
| 4,795,562 A | 1/1989 | Walsh |
| 4,840,714 A | 6/1989 | Littlehales |
| 4,874,691 A | * 10/1989 | Chandler ................... 422/101 |

(List continued on next page.)

FOREIGN PATENT DOCUMENTS

| | | |
|---|---|---|
| EP | 0 139 373 A1 * | 5/1985 |
| EP | 0 525 723 A2 | 2/1993 |
| WO | WO 98/20353 | 5/1998 |
| WO | WO 98/41863 | 9/1998 |
| WO | WO 00/45168 | 8/2000 |

OTHER PUBLICATIONS

Pappalardo et al. Microdissection, microchip arrays, and molecular analysis of tumor cells (Primary and Metastases). Seminars in Radiation Oncology (1998) vol. 8, No. 3, pp. 217–223.*

Cleeve et al., "Isoelectric focusing of human tissue alkaline phosphatase isoenzymes in agarose gel," *Clinica Chimica Acia*, 137:333–340 (1984).

van der Sluis et al., "Immunochemical detection of peptides and proteins on press–blots after direct tissue gel isoelectric focusing," *Electrophoresis*, 9:654–661 (1988).

(List continued on next page.)

*Primary Examiner*—Long V. Le
*Assistant Examiner*—Kartic Padmanabhan
(74) *Attorney, Agent, or Firm*—Klarquist Sparkman, LLP

(57) ABSTRACT

The present invention is directed to a device and a method for detecting biomolecules in a tissue section or other two-dimensional sample by creating "carbon copies" of the biomolecules eluted from the sample and visualizing the biomolecules on the copies using antibodies or DNA probes having specific affinity for the biomolecules of interest. Thin membranes in a stacked or layered configuration are applied to the sample, such as a tissue section, and reagents and reaction conditions are provided so that the biomolecules are eluted from the sample and transferred onto each of the stacked membranes thereby producing multiple replicas of the biomolecular content of the sample.

32 Claims, 7 Drawing Sheets

U.S. PATENT DOCUMENTS

| | | | | |
|---|---|---|---|---|
| 5,047,135 | A | | 9/1991 | Nieman ................. 204/299 R |
| 5,057,438 | A | * | 10/1991 | Imai et al. ................. 204/456 |
| 5,078,853 | A | | 1/1992 | Manning et al. ........ 204/299 R |
| 5,155,049 | A | | 10/1992 | Kauvar et al. |
| 5,173,159 | A | | 12/1992 | Dutertre |
| 5,238,651 | A | | 8/1993 | Chuba ......................... 422/61 |
| 5,332,484 | A | | 7/1994 | Hilt ............................ 204/301 |
| 5,387,325 | A | | 2/1995 | Opplt ..................... 204/299 R |
| 5,427,664 | A | | 6/1995 | Stoev et al. ............ 204/182.3 |
| 5,438,128 | A | * | 8/1995 | Nieuwkerk et al. ......... 435/270 |
| 5,486,452 | A | | 1/1996 | Gordon et al. ................ 435/5 |
| 5,650,055 | A | | 7/1997 | Margolis .................... 204/518 |
| 5,716,508 | A | | 2/1998 | Starr .......................... 204/618 |
| 5,741,639 | A | | 4/1998 | Ensing et al. .................. 435/6 |
| 5,843,657 | A | | 12/1998 | Liotta et al. |
| 5,993,627 | A | | 11/1999 | Anderson et al. |
| 6,013,165 | A | | 1/2000 | Wiktorowicz et al. |
| 6,064,754 | A | | 5/2000 | Parekh et al. |
| 6,087,134 | A | | 7/2000 | Saunders ................... 435/91.2 |
| 6,135,942 | A | | 10/2000 | Leptin |
| 6,232,067 | B1 | * | 5/2001 | Hunkapiller et al. ........... 435/5 |

OTHER PUBLICATIONS

Schumacher et al., "Direct tissue isoelectric focusing on ultrathin polyacrylamide gels. Applications in enzyme, lectin and immunohistochemistry," *Histochemical Journal*, 22:433–438 (1990).

Schumacher et al., "Direct Tissue Isoelectric Focusing on Mini Ultrathin Polyacrylamide Gels followed by Subsequent Western Blotting, Enzyme Detection, and Lectin Labeling as a Tool for Enzyme Characterization in Histochemistry," *Analytical Biochemistry*, 194:256–258 (1991).

Inczédy–Marcsek et al. "Extraction of proteins within ultrathin–layer polyacrylamide electrophoresis (SDS–PAGE) and isoelectric focusing (PAGIF) of cryostat sections and tissue culture specimens," *Acta histochemica*, Suppl.–Band XXXVI, S. 377–394 (1998).

Englert et al. "Molecular profiling of human cancer: New opportunities," *Current Opinion Moecular Therapeutics*, 1(6):712–719 (1999).

Englert et al., "Layered Expression Scanning: Rapid Molecular Profiling of Tumor Samples," *Cancer Research*, 60:1526–1530 (2000).

Braun and Abraham, "Modified diffusion blotting for rapid and efficient protein transfer with PhastSystem," *Electrophoresis* 10:249–253, 1989.

Demczuk et al., "Identification and analysis of all components of a gel retardation assay by combination with immunoblotting," *Proc. Natl. Acad. Sci. USA* 90:2574–2578, Apr. 1993.

Heukeshoven and Dernick, "Effective blotting of ultrathin polyacrylamide gels anchored to a solid matrix," *Electrophoresis* 16:748–756, 1995.

Legocki and Verma, "Multiple Immunoreplica Techique: Screening for Specific Proteins with a Series of Different Antibodies Using One Polyacrylamide Gel," *Anal. Biochem.* 111:385–392, 1981.

Manabe et al., "An Electroblotting Apparatus for Multiple Replica Technique and Identification of Human Serum Proteins on Mciro Two–Dimensional Gels," *Anal. Biochem.* 143:39–45, 1984.

Neumann and Müllner, "Two replica blotting methods for fast immunological analysis of common proteins in two–dimensional electrophoresis," *Electrophoresis* 19:752–757, 1998.

Olsen and Wiker, "Diffusion blotting for rapid production of multiple identical imprints from sodium dodecyl sulfate polyacrylamide gel electrophoresis on a solid support," *J. Immunol. Methods* 220:77–84, 1998.

Snachez et al., "Simultaneous analysis of cyclin and oncogene expression using multiple monoclonal antibody immunoblots," *Electrophoresis* 18:638–641, 1997.

* cited by examiner

FIGURE 3
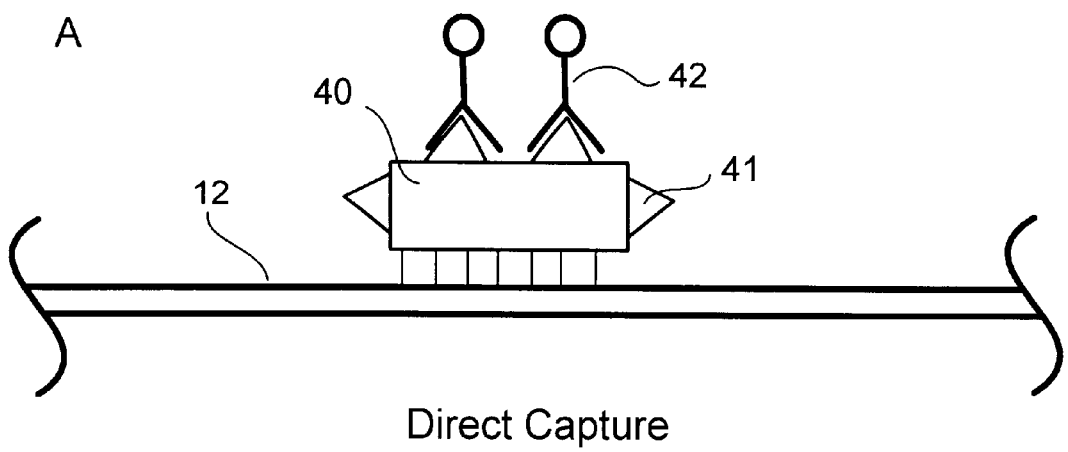
Direct Capture
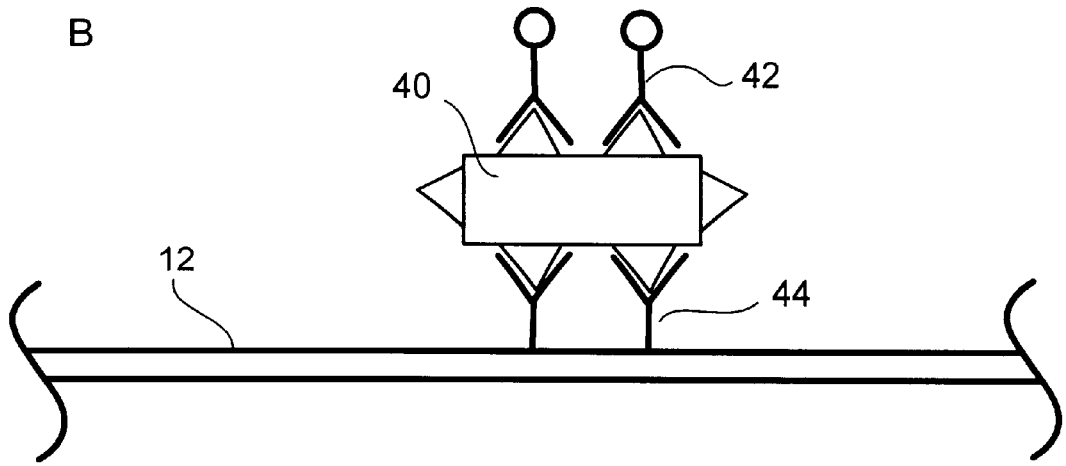
Indirect Capture

METHODS AND ARRAYS FOR DETECTING BIOMOLECULES

CROSS REFERENCE TO RELATED APPLICATIONS

This is a continuation-in-part of International Application No. PCT/US00/20354, filed Jul. 26, 2000, and claims the benefit of U.S. Provisional Application No. 60/145,613, filed Jul. 26, 1999.

STATEMENT OF GOVERNMENT RIGHTS

At least one of the inventors is an employee of an agency of the Government of the United States, and the government may have certain rights in this invention.

FIELD OF THE INVENTION

The present invention is directed to arrays for identifying large numbers of biomolecules in a biological sample so as to help determine their function and role in disease. More particularly, the invention relates to arrays of membranes for detecting and identifying large numbers of biomolecules in a multiplex manner. The application is a continuation-in-part of PCT application US00/20354 entitled Method and Production of Layered Expression Scans For Tissue and Cell Samples, which is incorporated herein by reference.

BACKGROUND OF THE INVENTION

Now that the 100,000 or so genes that make up the human genome have been sequenced, new tools are needed to determine when and in what type of tissue those genes are active so as to ascertain their function and role in disease. This effort, often referred to as "functional genomics" and "proteomics," is especially important in efforts to discover new drugs since most new pharmaceutical agents are being designed to target enzymes, receptors, and other proteins. Eventually, this information will be used in clinical diagnostics to help guide treatment selection in the emerging era of "personalized medicine."

Some believe that the 100,000 human genes may turn out to produce up to a million different protein variants. Of these, it is estimated that about 10,000 proteins will be identified over the next ten years as targets of pharmaceutical intervention. However, only a small fraction of these proteins are expressed in any particular tissue type. For example, a very different set of genes is expressed in brain tissue from those expressed in kidney even though cells in both organs have the same set of genes. Moreover, the subset of genes expressed in a kidney tumor differ from those active in healthy tissue from that organ. It is clear, therefore, that tools are needed to identify the activity of large numbers of genes in tissue samples removed from subjects.

To meet this need a number of "multiplex" assays have been introduced.

Among the most common type of assays for surveying the expression of large numbers of genes in parallel are DNA microarrays (a/k/a "biochips"). Most microarrays consist of a glass slide or other solid surface upon which thousands of cDNA probes are anchored. With these devices DNA probes are arrayed in a grid-like format. Messenger RNAs are isolated from the samples of interest and allowed to hybridize to the probes anchored to the biochip revealing the profile of the genes expressed. Various scanners and software programs are used to profile the patterns of genes that are "turned on." Representative of this biochip approach is the GeneChip® system from Affymetrix, Inc. (Santa Clara, Calif.).

While there are many uses for the aforementioned DNA microarrays, there are several limitations. First, they do not detect proteins, only nucleic acids. Since mRNA and protein levels do not always correlate in the cell and many regulatory processes occur after transcription, a direct measure of proteins is more desirable. Thus, since mRNA and protein levels do not always correlate in the cell and many functional protein modifications occur after translation, a direct way to monitor proteins is needed.

Another disadvantage of the microarrays known in the art is the fact that the sample being tested is disassociated from the tissue from which it was isolated. Disease is the result of disturbed biological equilibrium in groups of cells. Thus, it is often desirable to observe gene expression patterns in the context of the tissue in which the genes are active. In situ detection and visualization of proteins traditionally has been accomplished through immuno-histochemistry (IHC). This technique involves mounting a thin tissue section on the glass slide and visualizing a protein of interest with a detectable antibody that has specific binding affinity for the target protein. Because of certain technical limitations of IHC, only one or two proteins from a single tissue section can be analyzed. Also, proteins are still embedded in the tissue and are not presented to the antibodies in the most appropriate way (proteins are not highly denatured) lowering the success rate of the antibody reactivity.

Additionally microarrays known in the art require that in order to collect enough of the material for analysis, the sample being tested be a mixture of a number of different cell types (diseased tissue and adjacent normal cells) that are disassociated together and used for biomolecule extraction. As the result of this approach, biomolecules originating in the diseased tissue (e.g. tumor) are diluted and harder to detect and characterize. Since the morphological relationship is not preserved, it is hard to know what component of the sample is responsible for the changes observed in gene expression.

It is therefore desirable to have a method and device that combines the morphological advantages of IHC and other in-situ approaches with the multiplex and high-throughput characteristics of DNA microarrays.

To meet this need, Englert, et al. describe a very innovative technique which they refer to as "layered expression scanning" for molecular analysis of tumor samples that uses a layered array of capture membranes coupled to antibodies or DNA sequences to perform multiplex protein or mRNA analysis. *Cancer Research* 60, 1526–1530, Mar. 15, 2000. With this technique cell or tissue samples are transferred through a series of individual capture layers, each linked to a separate antibody or DNA sequence. As the biomolecules traverse the membrane set, each targeted protein or mRNA is specifically captured by the layer containing the corresponding antibody or cDNA sequence. The two-dimensional relationship of the cell populations is maintained during the transfer process thereby producing a molecular profile of each cell type present.

It would be desirable to supplement and enhance the layered expression scanning technique described by Englert, et al. with an approach that utilizes a stack of "blank" membranes that are not specific for any particular target. Instead, such membranes would ubiquitously bind to all (or a subset) of the biomolecules in a sample so as to give the user the flexibility of detecting a wide variety of biomolecules in an open format.

SUMMARY OF THE INVENTION

The present invention is directed to a device and a method for detecting biomolecules in a tissue section or other two-dimensional sample by creating "carbon copies" of the biomolecules eluted from the sample and visualizing the biomolecules on the copies using detectors, for example antibodies or DNA probes, having specific affinity for the biomolecules of interest.

Thin membranes in a stacked or layered configuration are applied to the sample, such as a tissue section, and reagents and reaction conditions are provided so that the biomolecules are eluted from the sample and transferred onto each of the stacked membranes thereby producing multiple substantial replicas of the biomolecular content of the sample. The treated membranes (or layers) are then separated. Each membrane is incubated with one or more different detectors (for example antibodies) specific for a particular biomolecule (such as a protein) of interest. The detectors employed are labeled or otherwise detectable using any of a variety of techniques such as chemiluminescence.

In an example in which proteins are detected, each membrane has essentially the same pattern of proteins bound to it, but different combinations of proteins are made visible on each membrane due to the particular antibodies selected to be applied. For example, one membrane layer may display proteins involved in programmed cell death (apoptosis) while an adjacent layer may display enzymes involved in cell division such as tyrosine kinases. In addition to proteins, nucleic acids may be targeted by using labeled DNA probes in lieu of antibodies. Moreover, different types of target biomolecules may be detected in different layers. For example, both protein and nucleic acid targets can be detected in parallel by applying both antibodies and probes to different layers of the array.

Another feature of the present invention is providing a kit that includes a group of membranes in a stack or other configuration that permits them to be stacked, and different detectors, such as cocktails of antibodies or probes, to be applied to the treated membranes for biomolecule detection.

With the foregoing and other objects, advantages and features of the invention that will become hereinafter apparent, the nature of the invention may be more clearly understood by reference to the following detailed description of the invention, the appended claims and to the several views illustrated in the drawings.

BRIEF DESCRIPTION OF THE DRAWINGS

FIG. 3 is a schematic illustration comparing direct and indirect capture.

FIG. 4A shows scanned images of the membranes incubated in protein comparing the intensity of signal and FIG. 4B is a chart plotting the amount of protein bound to different membrane materials.

FIG. 5A shows transfer through polycarbonate membranes. FIG. 5B shows transfer through polycarbonate coated with nitrocellulose. FIG. 5C shows transfer through polycarbonate coated with poly-L-lysine membranes.

DETAILED DESCRIPTION OF THE INVENTION

Definitions

"Biomolecules" means molecules typically produced by living organisms including peptides, proteins, glycoproteins, nucleic acids, fatty acids, and carbohydrates.

"Sample" means a material which contains biomolecules including tissue, gels, bodily fluids, and individual cells in suspensions or in pellet, as well as materials in containers of biomolecules such as microtiter plates.

"Captor" means a molecule, such as an antibody or DNA probe, that is anchored to a membrane and has an affinity (such as a specific affinity) for one of the biomolecules.

"Direct capture" means the conjugation or binding of a biomolecule directly onto the surface of the membrane without the aid of a captor antibody or the like.

"Indirect capture" means the conjugation or binding of a biomolecule onto a captor antibody or the like which in turn is bound to the surface of the membrane. Thus, with indirect capture the biomolecule is not directly conjugated to the membrane.

"Array" means two or more.

"Affinity" means the chemical attraction or force between molecules.

"Capacity" means the ability to receive, hold, or absorb biomolecules from the sample.

"Detector" means a molecule, such as an antibody or DNA probe, that is free in solution (i.e. not anchored to a membrane) and has an affinity for one of the sample components.

"Antibody cocktails" means mixtures of between two to about 100 different detector antibodies.

"Identical" means having substantially the same affinity for biomolecules.

"Membrane" means a thin sheet of natural or synthetic material that is porous or otherwise at least partially permeable to biomolecules.

"Stack" refers to adjacent substrates, whether stacked horizontally, vertically, at an angle, or in some other direction. The substrates may be spaced or touching, for example contiguous.

Figure 1:
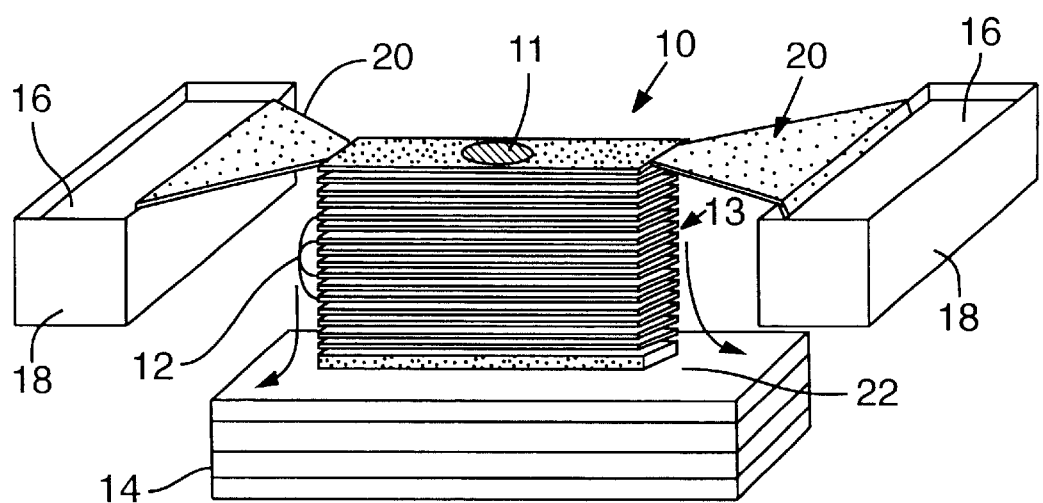
FIG. 1 is a perspective view of the membrane array according to the present invention shown transferring molecules from a tissue section.

The specific example illustrated in FIG. 1 shows a device and a method for detecting biomolecules in a tissue section 11 or other two-dimensional sample by creating "carbon copies" (substantial copies that are not necessarily identical copies, they may have slight differences but can be identical or nearly identical) of the biomolecules eluted from the sample, and visualizing the biomolecules on the copies using antibodies or other molecules having specific affinity for the biomolecules of interest. Thin membranes 12 in a stacked or layered configuration are brought into contact with the sample and reagents, and reaction conditions are provided so that the biomolecules are eluted from the sample onto the membranes, whereupon the biomolecules can be visualized using a variety of techniques, as set forth herein.

Certain examples of the invention include a method of detecting an analyte in a biological sample using stacked contiguous layered membranes that permit biomolecules to move through a plurality of the membranes, while directly capturing the biomolecules on one or more of the membranes. Biomolecules from the sample are moved through the membranes under conditions that allow one or more of the membranes to directly capture the biomolecules, and biomolecules of interest are concurrently or subsequently detected on the membranes, for example by exposing the biomolecules of interest to a detector, such as a specific capture molecule (for example an antibody or a nucleic acid probe).

Alternatively, the biomolecule itself may be a detector (such as a nucleic acid probe) to which a sample is exposed. In this case, the biological sample is one or more purified nucleic acid probes placed in assigned locations on a surface of the stack, which are allowed to migrate through membranes (for example in a direction of movement transverse to the layers) to produce multiple substantial "copies" of the original probes in corresponding locations on the multiple membranes. The layers can then be separated and exposed to a target biological specimen which may have nucleic acid molecules that hybridize to the probes.

In some examples, the biological sample is a tissue specimen that is placed on the stack of layered membranes, and biomolecules from the tissue specimen are directly captured by the membranes as the biomolecules move through the membranes. The membranes may, for example, be separated prior to detecting the biomolecules of interest, and the separated membranes are exposed to the detectors. Alternatively, the biological molecules of interest may be contained in a biological specimen to which the membranes are exposed. For example, the biomolecules directly captured by the membranes may themselves be nucleic acid probes or antibodies, and the membranes may be exposed to a biological specimen in which a nucleic acid or peptide (such as a protein) is to be detected.

In particular embodiments, the membranes comprise a material that non-specifically increases the affinity of the membranes to the biological molecules (or a class of biomolecules such as proteins or nucleic acids) that are moved through the membranes. For example, the membranes may be dipped in, coated with, or impregnated with nitrocellulose, poly-L-lysine, or mixtures thereof. In certain examples the membranes are not treated with a material that blocks the non-specific binding of the biomolecules to the membranes, at least during transfer of the biomolecules through the membranes. However, in other embodiments, some such blocking agents can be added to the membranes, as long as the amount of blocking agent minimizes the amount of biomolecules bound, without blocking it altogether. In certain examples, blocking agent may be added to the membranes after transfer of the biomolecules through the membranes, but before or during exposure to the detectors.

In particular examples, the membranes are sufficiently thin to allow the biomolecules to move through the plurality of membranes (for example 10, 50, 100 or more) in the stack. Such membranes, for example, have a thickness of less than 30 microns. The membranes may be made of a material that does not substantially impede movement of the biomolecules through the membranes, such as polycarbonate, cellulose acetate, or mixtures thereof.

The material of the membranes may-maintain a relative relationship of biomolecules as they move through the membranes, so that the same biomolecule (or group of biomolecules) move through the plurality of membranes at corresponding positions. In such examples, this coherence of relative relationships allows the different membranes to be substantial "copies" of one another, much like a "carbon copy" would be. However, like a "carbon copy" there may be some differences between the different "copies" present in the different membranes.

In particular embodiments, a transfer liquid (such as a buffer) is passed through the membranes to encourage movement of the biomolecules through them. A distal or downstream wick may also be provided to help move liquid (such as the buffer) through the membranes in a desired direction of movement.

Biomolecules detected on the membrane copies may be correlated with a biological characteristic of the sample. For example, a tissue specimen may be placed in a position on top of the stack, and a biomolecule of interest (such as a particular protein) may be detected in one of the membrane copies at a position that corresponds to the position in which the tissue specimen (or one of its substructures such as an organelle) was placed. The presence of that biomolecule in the tissue specimen can then be correlated with a biological characteristic of the sample. For example, a highly malignant tissue specimen may be found to contain a protein, that may then be associated with the highly malignant phenotype of the specimen.

Other embodiments of the invention can include kits which contain a membrane array for detecting biomolecules (such as proteins or nucleic acids) in a sample. The array includes a plurality of membranes, each of which has a non-specific or substantially same affinity for the biomolecules. The kit also includes containers of antibodies or probes (or mixtures of antibodies, mixtures of probes, or mixtures of the antibodies and probes) for detecting biomolecules captured on each membrane. In particular examples of the kit, the membranes are polymer substrates containing or coated with a material (such as nitrocellulose) for increasing an affinity of the substrate to the biomolecules.

In particular examples, the method can be used to create a set of microarray substantial "copies" by applying a plurality of detectors, such as DNA probes, antibodies, or a combination thereof, to the stack of layered membranes. The stack of layered membranes provide a plurality of substrates through which the probes or antibodies move, and in which a portion of the probes or antibodies are directly captured by one or more of the substrates. The substrates can be subsequently separated to provide corresponding substrates having a plurality of DNA probes, antibodies or a combination thereof, in corresponding positions of each of said substrates. The multiple membranes maintain a substantially coherent relationship between the probes and/or antibodies as they move through the substrate. This coherent relationship may or may not be a direct spatial correspondence, but the relative relationship between the biomolecules may be maintained in such a way that the identity of the biomolecules on the membranes can be known from the relationship in which the biomolecules were placed on the stack of layered membranes.

In particular embodiments, the plurality of DNA probes, antibodies, or combination thereof, is applied to the stack of membranes from a plate having a plurality of wells, each containing a different DNA probe or antibody. The DNA probes or antibodies are transferred from the wells to the stack so as to create a set of substantially replicate microarrays.

Referring now in detail to the drawings of specific, non-limiting detailed examples wherein like parts are designated by like reference numerals throughout, there is illustrated in FIG. 1 a perspective view of the membrane array apparatus according to the present invention designated generally by reference numeral 10. Apparatus 10 includes a plurality of membranes 12 shown in a layered or stacked configuration such as array 13. While only about a dozen membranes are shown in FIG. 1 it should be appreciated that many more membranes (e.g., 10, 50, 100 or more) may be employed depending on the number of targets sought to be identified, the quantity of biomolecules present in the sample, and the thickness of the material employed to construct membranes 12. Optionally, membranes 12 may be packaged in a suitable sealed enclosure or frame (not shown) to maintain their integrity and prevent contamination.

Membrane array 13 is placed atop a stack of blotting paper 14 that acts as a lower wick pulling buffer out of buffer chambers 18 though upper wicks 20 and membrane array 12 in the direction of the arrows shown in FIG. 1. A biomolecule trap 22 is positioned intermediate membrane array 12 and blotting paper 14 to help the user ascertain whether proper transfer has occurred.

Figure 2:
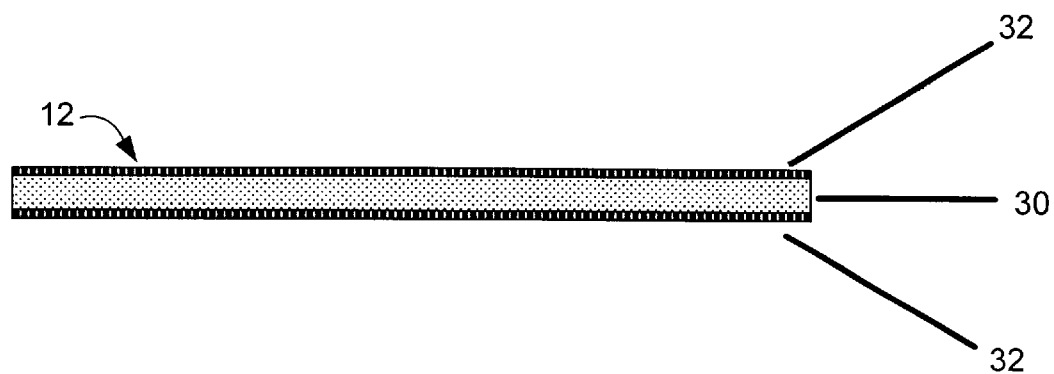
FIG. 2 is a longitudinal sectional view of an individual membrane according to the present invention.

With reference to FIG. 2, individual membranes 12 are constructed of a porous substrate 30 coated with a material which increases the affinity of the membrane to the biomolecules being transferred. Substrate 30 is, for example, constructed of polycarbonate or a similar polymeric material that maintains sufficient structural integrity despite being made porous and very thin. However, in lieu of polycarbonate the substrate 30 may for example be constructed of cellulose derivatives such as cellulose acetate, as well as polyolefins, (e.g. polyethelyle, polypropylene, etc.). It is a particular feature of the present invention that membranes 12 have a high affinity for proteins and other biomolecules, but have a low capacity for retaining such molecules. This feature permits the molecules to pass through the membrane stack with only a limited number being trapped on each of the successive layers thereby allowing multiple "carbon copies" to be generated. In other words, the low capacity allows the creation of multiple replicates as only a limited quantity of the biomolecules are trapped on each layer. If a membrane were used that had a high binding capacity for biomolecules-such as the transfer membranes conventionally used with gel blotting-multiple replicas could not be made.

To maintain the binding capacity of membrane 12 sufficiently low to avoid trapping of too much of the sample, the thickness of substrate 30 is, for example, less than about 30 microns, and in particular embodiments is between about 4–20 microns, for example between about 8 to 10 microns. The pore size of the substrate is, for example, between about 0.1 to 5.0 microns, such as about 0.4 microns. Another advantage of using a thin membrane is that is lessens the phenomenon of lateral diffusion. The thicker the overall stack, the wider the lateral diffusion of biomolecules moving through the stack.

The illustrated substrate 30 includes a coating 32 on its upper and lower surfaces to increase non-specific binding of the proteins or other targeted biomolecules. Although the binding to the coating is "non-specific" in the sense that it does not recognize particular proteins or other biomolecules, such as particular nucleic acids, it may be specific in that it recognizes and specifically binds classes of biomolecules, such as proteins or nucleic acids, or combinations thereof. Coating 32 in the disclosed embodiment is nitrocellulose, but other materials such as poly-L-lysine may also be employed. Before being applied to substrate 30, the nitrocellulose is dissolved in methanol or other appropriate solvent in concentration from 0.1%–1.0%. The membranes are immersed in this solution as described more fully in the Examples, below. In lieu of coating 32, nitrocellulose or other materials with an affinity for biomolecules can be mixed with the polycarbonate before the substrate is formed thereby providing an uncoated substrate having all of the desired characteristics of the membrane. Alternative coating methods known in the art may be used in lieu of dip coating including lamination. Alternatively, only one surface may be coated, such as the surface that faces the sample, instead of both surfaces.

It is a particular feature of the present invention that membranes 12 have a high affinity for proteins and other biomolecules, but have a low capacity for retaining such molecules. This feature permits the molecules to pass through the membrane stack with only a limited number being trapped on each of the successive layers thereby allowing multiple "carbon copies" to be generated. In other words, the low capacity allows the creation of multiple substantial replicates as only a limited quantity of the biomolecules are trapped on each layer. If a membrane were used that had a high binding capacity for biomolecules-such as with nitrocellulose membranes conventionally used with gel blotting-multiple replicas could not as easily be made. More specifically, the affinity and capacity of membrane 12 should be such that when at least 5 and preferably more than 10 membranes are stacked and applied to a sample according to the disclosed method, most of the biomolecules of interest can be detected on any and all of the membranes including those positioned furthest from the sample.

With reference to FIG. 3, the aforementioned technique may be described as "direct capture" since the target biomolecules 40 are captured directly on the surface of membranes (or within the membrane), instead of being captured indirectly by a binding agent (such as an antibody or nucleic acid probe) applied to the membrane. During this disclosed process different components of the sample bind to the membrane with the same affinity, but directly proportional to their concentration in the sample (a component with a higher concentration will leave more molecules on each membrane, and a component with a lower concentration will leave less molecules on each membrane). A detector molecule 42, such as a labeled antibody that specifically binds to the biomolecule 40, may be utilized to detect biomolecule bound to the membrane. In examples in which the amount of a component bound to the membrane is proportional to the amount of the component in the sample, an amount of the detector molecule can be correlated to an amount (or relative amount) of the biomolecule detected.

In order to achieve high affinity and high capacity for a particular group of biomolecules from a sample, coating of the membranes with a captor molecule 44 is performed in the method described by Englert et al. (supra.). This may be referred to as "indirect capture" and is illustrated in FIG. 4B. Captor 44 can be cDNA, antibody, or any other protein specific for the target of interest. Single-stranded cDNA molecules generated by number of means (Polymerase Chain Reaction, nick translation, reverse transcription, oligonucleotide synthesis) or proteins (like immunoglobulin) can be directly attached to the membrane. Alternatively, the linker-arms that would allow spatial control of the captor binding could be directly attached to the membrane followed by captor attachment to them. This will expose the majority of the active target recognition sites increasing that way capacity of the indirect capture. Streptavidin coated membranes may be employed to bind end-biotinilated nucleic acids and randomly biotinilated proteins, or protein A and protein G to bind immunoglobulins.

In use and operation, apparatus 10 may be employed to create "carbon copies" or substantial replicas of the biolmolecular contents of the sample applied to the stack. Membranes 12 are arrayed in a layered or stacked configuration as shown in FIG. 1 as reference numeral 13. In a particular embodiment, a sample such as a conventional frozen tissue section 11 is placed on a layer of polycarbonate and then sandwiched between two slices of 2% agarose (not shown). The entire preparation is positioned adjacent to the membrane array. Buffer is applied using chambers 18 and wicks 20 to elute and transfer proteins from the frozen section. About 50–100 milliliters of buffer per square centimeter are used in each transfer with average length of the transfer being about 1–2 hours. After transfer the membranes are separated and incubated with the detector antibody. Antibodies are selected based on the types of targets sought. Membranes are washed in a buffer, and the protein/detector complex can be visualized using a number of techniques such as ECL, direct fluorescence, or colorimetric reactions. ECL is preferred. Commercially available flatbed scanners and digital imaging software can be employed to display the images according to the preference of the user.

It should be appreciated that because the size of the membrane array can be varied, the user has the option of analyzing a large number of different samples in parallel, thereby permitting direct comparison between different patient samples. For example different samples from the same patient at different stages of disease can be compared in a side-by-side arrangement as can samples from different patients with the same disease.

Figure 7:
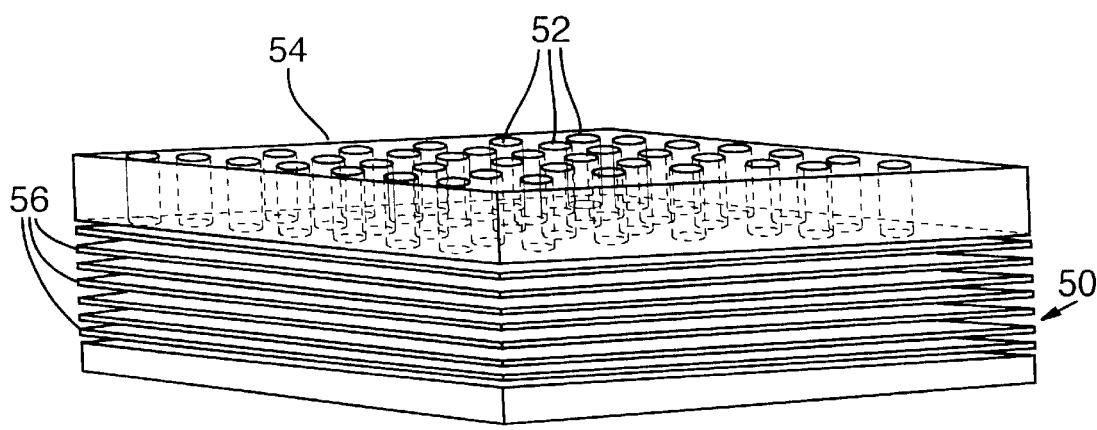
FIG. 7 is a perspective view of the array according to the present invention shown in use with a microtiter plate.

Another use of the membrane array according to the present invention is to make multiple copies of a cDNA microarray in a manner that is less expensive and laborintensive than robotic systems. With reference to FIG. 7, DNA sequences representing different genes are placed into individual microtiter wells 52 of a microtiter plate 54 (e.g. a 96-well plate). The microtiter plate 54 is placed adjacent to a stack of membranes 56 of the same construction as membranes 12, to allow the contents of the microtiter wells to be transferred from the respective wells to the stack of membranes 50. In the illustrated embodiment, the contents of the wells are transferred from the wells 52 to a top surface of the stack of membranes 56, so that the contents are applied in a pattern that corresponds to a pattern of the wells.

The DNA is transferred through the membranes in a direction of movement from the wells toward a wick member 58, and the spatial orientation of the samples is maintained. Because of the high affinity, low capacity characteristics of membranes 56, as the nucleic acids traverse the capture membrane set 56, a small percentage of DNA hybridizes to each membrane, creating a series of replicate copies, each one containing a grid of DNA spots that match the orientation of the DNA samples in the microtiter plate. Thus, a set of cDNA arrays may be created in a very rapid and inexpensive fashion. Antibody and tissue lysate arrays can also be created by this method.

EXAMPLES

Example #1

Construction of the Polycarbonate Membrane Suitable for the Protein Binding

Figure 4:
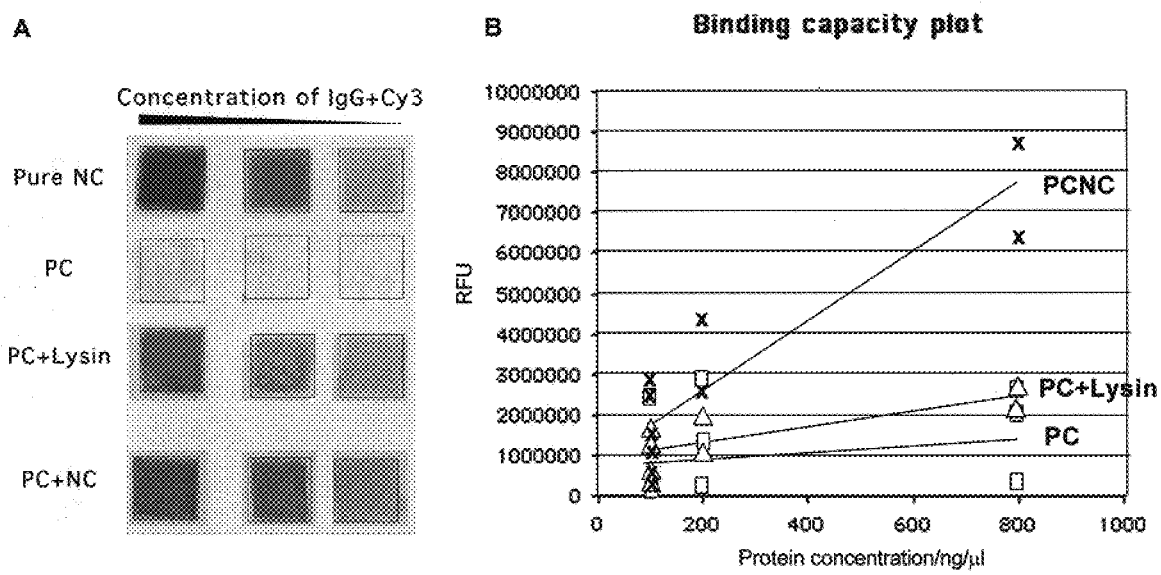
FIG. 4 is a schematic illustration comparing the binding capacity of membranes constructed of nitrocellulose and polycarbonate, both coated and uncoated.

Native, non-coated polycarbonate membrane (Millipore, Mass.) has low affinity and low binding capacity for proteins. To improve its protein binding characteristics, polycarbonate membranes were coated with either poly-L lysine (referred to as PC+Lysin in FIG. 4) or nitrocellulose (referred to as PC+NC in FIG. 4). Membranes (177 square centimeters) were immersed for 1 minute in 5 ml of either aqueous solution of 0.1% poly-L-lysine or 0.1–1.0% nitrocellulose solution in 100% methanol. After coating, membranes were suspended in vertical position and air-dried at room temperature for 5–10 minutes. Poly-L-lysine treated membranes were before use additionally baked for 2 hours at 50° C. Small squares (0.25 square centimeters) of both treated and non-treated membranes were incubated in TBST solution (50 mM TRIS pH 8.0, 150 mM NaCl and 0.05% Tween-20) with 1.0–100.0 ng/ul of goat immunoglobulin labeled with Cy3 fluorescent dye (Amersham Pharmacia Biotech, USA) for 0.5–2 hours at room temperature. Membranes were washed in TBST and examined on STORM scanner (Molecular Dynamics, USA). The results are shown in FIG. 4A. The intensity of the signal was quantified by ImageQuant (Molecular Dynamics, USA) and data points from five different experiments were plotted using Microsoft Excel. The results shown in FIG. 4B demonstrate that polycarbonate membranes have a low protein binding potential that can be considerably enhanced by coating the membrane with poly-L-lysine (PC+Lysin) or nitrocellulose (PCNC).

Example #2

Testing the Porosity of Prepared Polycarbonate Layers

Figure 5:
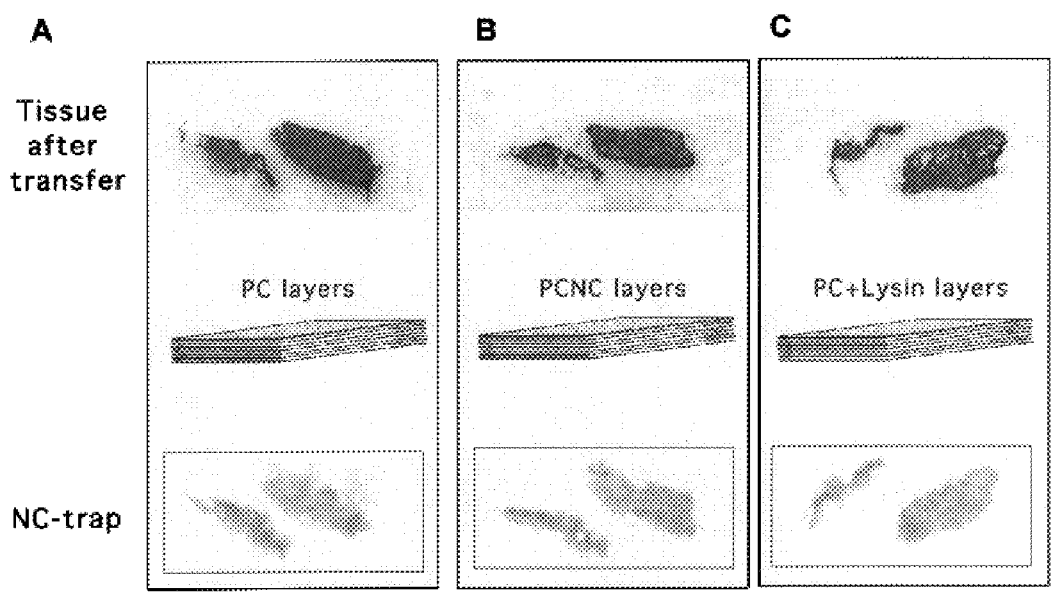
FIG. 5 are images of tissue sections that show that portions of total biomolecules can be successfully transferred through a stack of polycarbonate (PC) layers onto the trap.

To demonstrate porosity of manufactured layers, native, poly-L-lysine or nitrocellulose coated membranes were blocked in 5% bovine serum albumen solution in 50 mM TRIS pH 8.0 to prevent any protein binding. Fifty-one square centimeter pieces were cut out and stacked together to make a pile. A non-blocked pure nitrocellulose layer was used at the bottom to capture proteins (NC-trap). Three adjacent 20 micrometer thick frozen sections of normal breast tissue were collected on a polycarbonate membrane with 5.0 um pore size and embedded in a 2% agarose gel and transferred side by side through each stack. Between 50 and 100 milliliters of TBST buffer was used per square centimeter of the membrane stack with average length of the transfer being 1 hour. After transfer, proteins remaining in the tissue sections and total proteins on the NC-trap were visualized by Ponceau S staining (SIGMA, Mo.). As shown in FIG. 5, the outline of the total proteins transferred through the stack and trapped on the nitrocellulose layer very closely resembled the outline of the applied tissue section suggesting that not only were membranes porous enough to allow for the proteins to be transferred, but also that at least up to 50 polycarbonate membranes can be used in this kind of assay without apparent distortion of the image due to lateral diffusion.

Example #3

Demonstration of Low Capacity Protein Binding to the Nitrocellulose Coated Polycarbonate Layers Examples #1 and #2 demonstrate that proteins in solution can bind to a single nitrocellulose coated polycarbonate layer and that complete saturation of the layer with proteins does not affect its porosity. To ascertain how much of the total protein would be trapped on each individual layer during the tissue section transfer, 20 micron thick frozen sections of normal and tumor breast tissue were placed adjacent to each other on a polycarbonate membrane with 5.0 um pore size, embedded in 2% agarose gel and transferred through 14 layers of nitrocellulose coated polycarbonate to the NC-trap on the bottom, in 100 ml/cm2 of buffer containing 25 mM TRIS pH 8.3, 192 mM glycine, 0.05% SDS and 20% methanol. After transfer, proteins left over in the tissue sections were visualized by Ponceau S staining (SIGMA, U.S.A.) and total eluted proteins captured on the NC-trap were visualized by BLOT FastStain (Chemicon, USA). The image formed on the trap demonstrated successful transfer of the protein through the membranes.

To determine whether sufficient total protein trapped on each membrane during the transfer to perform immunological detection 14 arbitrarily selected antibodies were used. Antibodies were: Anti-GAPDH, 1:100 (Chemicon, MAB374); Anti-Rsk, 1:1,000 (Transduction Laboratories, R23820); Anti-Stat5a, 1:500 (Santa Cruz Biotechnology, sc-1081); Anti-IFNalpha, 1:500 (Biosource, AHC4814); Anti-RARalpha, 1:1,000 (Biomol, sa-178); Anti-phospho-EGFR, 1:1,000 (Upstate, 05-483); Anti-non-phospho EGFR, 1:1,000 (Upstate, 05-484); Anti-phospho-NR1, 1:500 (Upstate, 06-651); Anti-Stat1, 1:2,000 (Transduction Laboratories, G16920); Anti-Rb, 1:1,000 (Santa Cruz Biotechnology, sc-50); Anti-Jak1, 1:500 (Santa Cruz Biotechnology, sc-295); Anti-tubulin-alpha, 1:500 (Santa Cruz Biotechnology, sc-5546); Anti-beta-actin, 1:2,000 (SIGMA, A5441).

Figure 6:
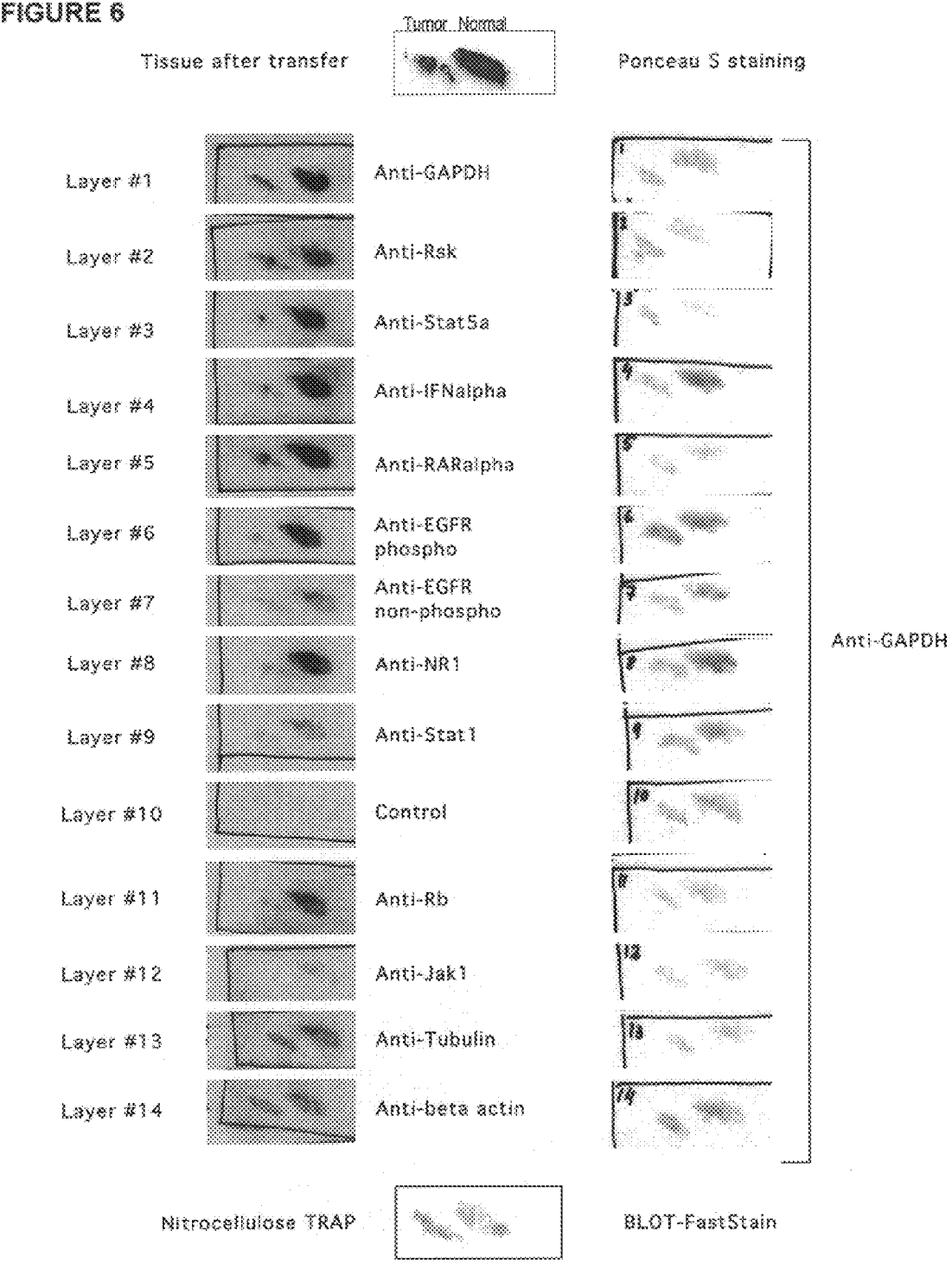
FIG. 6 is a series of images showing immunodetection of different proteins from two regions (healthy and cancerous) of a breast tissue using the membrane array according to the present invention.

Polycarbonate layers were first blocked in 1×casein solution (Vector Labs, U.S.A.) for 1 hour at room temperature and incubated overnight at +4° C. in primary antibodies as listed in FIG. 6 followed by TBST washes and incubation in alkaline phosphatase (AP) conjugated secondary antibodies (1:2,000 dilution) (Rockland, U.S.A.). Membranes were then incubated for 5 minutes in enhanced chemiluminescence substrate (ECL, Vector Labs, U.S.A.) followed by visualization of the protein by exposing the membranes to X-ray film (Kodak, U.S.A.).

The results showed that the method of this invention allows detection of number of different proteins. To ascertain how the membranes performed with respect to the amount of total protein captured, the membranes were each incubated with the same antibody, allowing determination of the protein content on each of them. Anti-GAPDH antibody was used for 3 hours at room temperature, washed in TBST, incubated with anti-mouse secondary antibody conjugated to horseradish peroxidase (HRP) and visualized in enhanced chemiluminescence substrate specific only for HRP (PIERCE, U.S.A.). After ECL reaction membranes were exposed to film as stated before. The results confirmed that all of the membranes did capture a similar portion of the total protein and differences seen in the first part of the experiment are not the result of differences in membrane "loading." For documentation purposes, the X-ray film was scanned on the flat bed scanner (Lacie, USA) and images were processed using ADOBE PhotoShop 4.0.

Although certain disclosed embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law. The references cited above are hereby incorporated herein in their entirety.

What is claimed is:

1. A method of making multiple substantial replicas of a biomolecular content of a sample, which method comprises:

providing a stack of membranes, wherein said membranes permit biomolecules applied to said stack to move through multiple of said membranes, while capturing at least a portion of said biomolecules on the multiple membranes; and applying said sample to said stack of membranes, under conditions that (a) allow at least a portion of said biomolecules to elute from the sample through the stack of membranes, and (b) allow said multiple membranes to capture at least a portion of said biomolecules from said sample, thereby forming said multiple substantial replicas of the biomolecular content of the sample, wherein the biomolecules have a relative relationship to each other in at least two dimensions within the sample, and wherein each of the substantial replicas maintains the relative relationship of the biomolecules.

2. The method of claim 1, further comprising detecting at least one biomolecule of interest on at least one of said multiple membranes.

3. The method of claim 2, wherein detecting biomolecules of interest comprises exposing at least one of said multiple membranes to a detector.

4. The method of claim 3, wherein the sample is a tissue specimen that is placed on said stack of membranes, and biomolecules from said tissue specimen are captured by said membranes as said biomolecules from said tissue specimen move through said multiple membranes.

5. The method of claim 3, further comprising separating said multiple membranes from each other and from the sample prior to detecting said biomolecules of interest.

6. The method according to claim 2 wherein each of said membranes comprises a porous substrate having a thickness of less than 30 microns and no less than 4 microns.

7. The method according to claim 6 wherein one or more of said membranes comprise a material for increasing an affinity of at least one of said membranes to the biomolecules.

8. The method of claim 7, wherein said material is coated on one or more of said membranes.

9. The method of claim 6 wherein said porous substrate comprises a material selected from the group consisting of polycarbonate, cellulose acetate, and mixtures thereof.

10. The method of claim 9, wherein said porous substrate is a polycarbonate substrate.

11. The method of claim 7, wherein said material for increasing affinity is selected from the group consisting of nitrocellulose, poly-L-lysine, and mixtures thereof.

12. The method according to claim 1 wherein said sample is a tissue section.

13. The method of claim 1, wherein detecting said biomolecules comprises separating one or more of said membranes from said stack, and detecting said biomolecules on one or more of the separated membranes.

14. The method of claim 1, wherein said conditions that permit movement of said biomolecules through said multiple membranes comprises passing a transfer liquid through said membranes.

15. The method of claim 1, wherein said conditions that permit movement of said biomolecules through one or more of said membranes comprises providing a wick that encourages movement of said biomolecules through said stack of membranes in a desired direction of movement.

16. The method of claim 1, wherein said stack of membranes comprises 50 or more of said membranes.

17. The method of claim 1, wherein said sample is a DNA sample.

18. The method of claim 1, further comprising correlating said biomolecules detected on said one or more membranes with a biological characteristic of said sample.

19. The method of claim 1 wherein the sample is a microarray, and the microarray comprises a plurality of DNA probes, antibodies or a combination thereof.

20. The method of claim 19, further comprising separating said substrates to provide corresponding substrates having a plurality of said DNA probes, antibodies or combination thereof, in corresponding positions on each of said substrates.

21. The method of claim 19, wherein the sample is applied to said stack from a plate having a plurality of wells each containing a different DNA probe or antibody, and said DNA probes or antibodies are transferred from said wells to said stack so as to create a set of substantially replicate microarrays.

22. The method of claim 19, wherein said stack of membranes comprises a plurality of substrates through which said probes or antibodies move, and in which a portion of said probes or antibodies are captured by one or more of said substrates.

23. A method of making multiple substantial replicas of a biomolecular content of a tissue section, comprising:
providing a plurality of membranes in a stacked or layered configuration;
providing a tissue section containing biomolecules, which biomolecules have a relative relationship to each other in at least two dimensions within the tissue section;
applying the tissue section to the plurality of membranes under conditions that allow multiple membranes to capture at least a portion of the biomolecules from the tissue section so as to create multiple substantial replicas of the biomolecular content of the tissue section, and wherein each of the substantial replicas maintains the relative relationship of the biomolecules.

24. A method of making multiple substantial copies of a biomolecular content of a biological sample, which method comprises:
providing a stack of membranes having a surface, wherein the membranes permit biomolecules applied to the stack to move through multiple of the membranes, while capturing at least a portion of the biomolecules on the multiple membranes; and
applying the biological sample to the surface of the stack of membranes, under conditions that (a) allow the biomolecules to elute from the biological sample transversely through the stack of membranes, and (b) allow the multiple membranes to capture at least a portion of the biomolecules, thereby forming the multiple substantial copies of the biological sample, wherein the biomolecules have a relative relationship to each other in at least two dimensions in the biological sample, and wherein each of the substantial copies maintains the relative relationship of the biomolecules of the biological sample.

25. The method of claim 24, wherein the biological sample is a tissue section, a gel, or an array.

26. A method of making multiple substantial replicas of a biomolecular content of a sample, the method comprising:
providing a plurality of membranes in a stacked or layered configuration;
providing a sample containing biomolecules oriented in at least two dimensions;
applying said sample to said plurality of membranes under conditions that allow multiple membranes to capture at least a portion of said biomolecules from said sample so as to create multiple substantial replicas of the biomolecular content of said sample, wherein the two dimensional orientation of the biomolecules on said membranes substantially corresponds to the two dimensional orientation of the molecules in said sample.

27. The method of claim 26, wherein said sample is a tissue section.

28. The method of claim 26, wherein said sample is a gel.

29. The method of claim 26, wherein said sample is contained in a microtiter plate.

30. The method of claim 26, further comprising removing the membranes having biomolecules captured thereon from said sample.

31. The method of claim 26, further comprising applying a different detector molecule to multiple of said membranes.

32. The method of claim 31, further comprising separating said multiple membranes prior to applying said detector molecules.

* * * * *